(12) United States Patent
Nemoto

(10) Patent No.: US 7,331,938 B2
(45) Date of Patent: Feb. 19, 2008

(54) MEDICINE LIQUID INJECTION DEVICE WHERE MEDICINE LIQUID SUCKED UP FROM MEDICINE LIQUID TANK AND INJECTED TO SUBJECT DOES NOT FLOW BACK

(75) Inventor: Shigeru Nemoto, Tokyo (JP)

(73) Assignee: Nemoto Kyorindo Co. Ltd., Tokyo (JP)

( * ) Notice: Subject to any disclaimer, the term of this patent is extended or adjusted under 35 U.S.C. 154(b) by 0 days.

(21) Appl. No.: 10/523,739

(22) PCT Filed: Aug. 6, 2003

(86) PCT No.: PCT/JP03/09972

§ 371 (c)(1),
(2), (4) Date: Feb. 4, 2005

(87) PCT Pub. No.: WO2004/014478

PCT Pub. Date: Feb. 19, 2004

(65) Prior Publication Data

US 2005/0245873 A1    Nov. 3, 2005

(30) Foreign Application Priority Data

Aug. 8, 2002 (JP) .............................. 2002-231160

(51) Int. Cl.
*A61M 37/00* (2006.01)
(52) U.S. Cl. ...................... 604/131; 604/151
(58) Field of Classification Search ........ 604/245–248, 604/218, 131, 140–141, 151–152, 118–121, 604/133, 143–144, 146, 147, 154, 256–259; 600/431, 432, 420, 3, 4, 434
See application file for complete search history.

(56) References Cited

U.S. PATENT DOCUMENTS

| | | | |
|---|---|---|---|
| 5,334,170 A | * | 8/1994 | Moroski ....................... 604/80 |
| 6,017,332 A | | 1/2000 | Urrutia |
| 6,302,864 B1 | * | 10/2001 | Nowosielski ................ 604/65 |

(Continued)

FOREIGN PATENT DOCUMENTS

JP           1-147841         10/1989

(Continued)

*Primary Examiner*—Nicholas Lucchesi
*Assistant Examiner*—Theodore J. Stigell
(74) *Attorney, Agent, or Firm*—Knobbe, Martens, Olson & Bear, LLP

(57) ABSTRACT

The present invention provides liquid injector 100 wherein syringe 210 sucks a liquid from liquid tank 200 in a suck state in which connection switch mechanism 105 connects syringe tube 103 to tank tube 102, and syringe 210 injects the liquid into a patient in an injection state in which connection switch mechanism 105 connects syringe tube 103 to patient tube 101. Since connection switch mechanism 105 blocks patient tube 101 in the suck state, the liquid does not flow back into syringe 210 from the patient. Since tank tube 102 is blocked in the injection state, the liquid does not flow back into liquid tank 200 from syringe 210. Therefore, it is possible to provide liquid injector 100 capable of preventing a backflow of the liquid from the patient to syringe 210 or liquid tank 200 in the structure in which syringe 210 sucks and injects the liquid from liquid tank 200 into the patient.

13 Claims, 10 Drawing Sheets

U.S. PATENT DOCUMENTS

| | | | |
|---|---|---|---|
| 6,371,942 B1 * | 4/2002 | Schwartz et al. | 604/246 |
| 6,471,674 B1 * | 10/2002 | Emig et al. | 604/131 |
| 6,650,929 B1 * | 11/2003 | Nemoto et al. | 600/431 |
| 6,866,654 B2 * | 3/2005 | Callan et al. | 604/247 |
| 6,945,959 B2 * | 9/2005 | Duchon et al. | 604/131 |
| 2001/0044618 A1 * | 11/2001 | Recinella et al. | 604/507 |

FOREIGN PATENT DOCUMENTS

| | | | |
|---|---|---|---|
| JP | 147841/1989 | * | 10/1989 |
| JP | 3-82462 A | | 4/1991 |
| JP | 03082462 A | * | 4/1991 |
| JP | 3-292964 A | | 12/1991 |
| JP | 03292964 A | * | 12/1991 |
| JP | 5-293170 A | | 11/1993 |
| JP | 2001-339707 | * | 11/2001 |
| JP | 2003-199823 A | | 7/2003 |
| WO | WO 3039644 A1 | * | 5/2003 |
| WO | WO 3039644 A1 | * | 5/2003 |

* cited by examiner

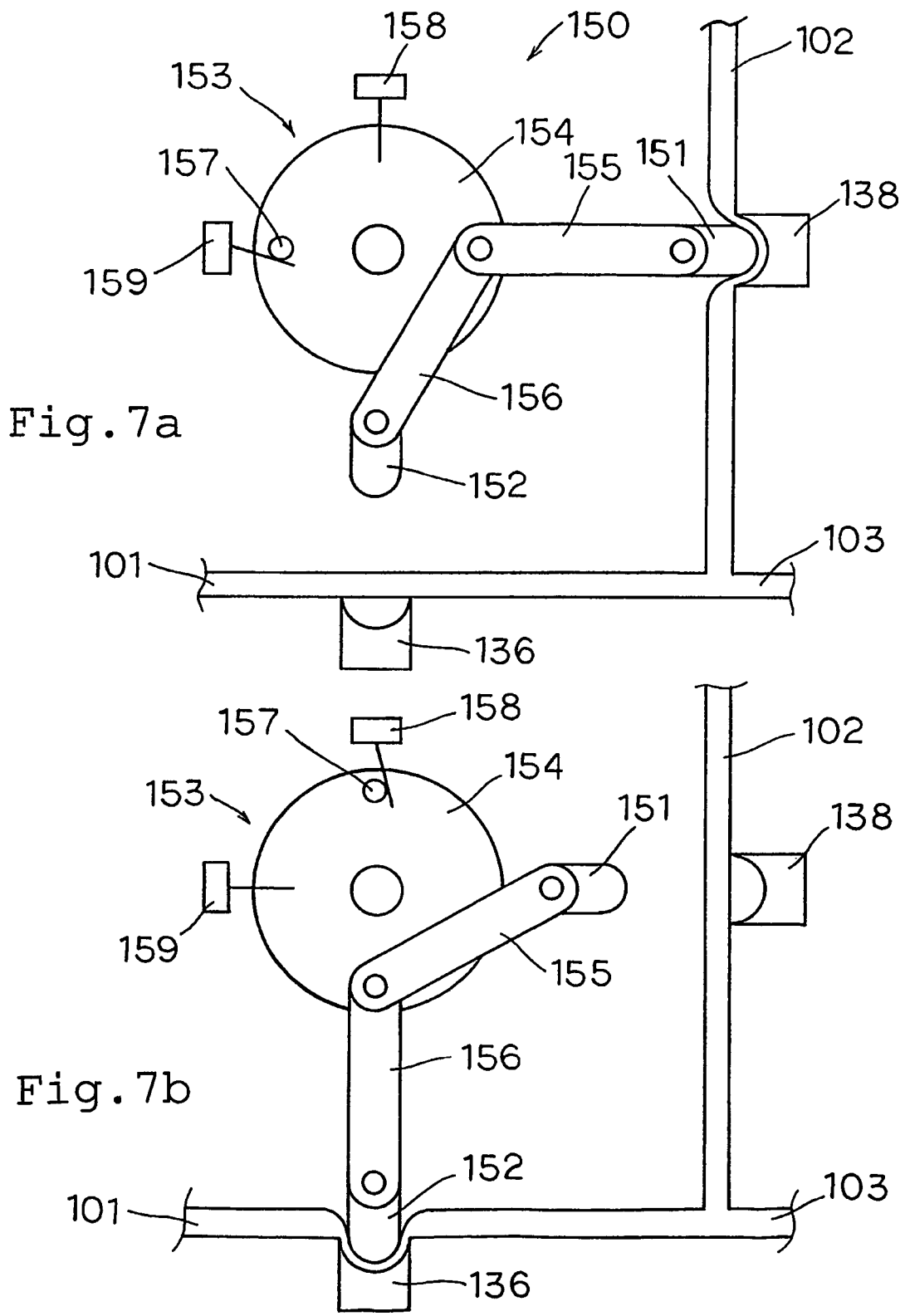

MEDICINE LIQUID INJECTION DEVICE WHERE MEDICINE LIQUID SUCKED UP FROM MEDICINE LIQUID TANK AND INJECTED TO SUBJECT DOES NOT FLOW BACK

This application is the U.S. National Phase under 35 U.S.C. §371 of International Application PCT/JP2003/009972, filed Aug. 6, 2003, which claims priority to Japanese Patent Application No. 2002-231160, filed Aug. 8, 2002. The International Application was not published under PCT Article 21(2) in English

TECHNICAL FIELD

The present invention relates to a liquid injector for injecting a liquid into a patient, and more particularly, to a liquid injector in which a syringe having a cylinder member and a piston member inserted slidably into the cylinder member is used to suck a liquid from a liquid tank and inject the liquid into a patient.

BACKGROUND ART

Currently, CT (Computed Tomography) scanners used in medical facilities can create cross-sectional images of a patient by the application of X-ray imaging. MRI (Magnetic Resonance Imaging) apparatuses can create cross-sectional images of a patient in real time with the magnetic resonance effect. Angiographic apparatuses can image blood vessels of a patient by the application of the X-ray imaging.

When the abovementioned apparatuses are used, a patient may be injected with a liquid such as a contrast medium and saline. Liquid injectors for automatically performing the injection have been put into practical use. Such a liquid injector has an injection head on which a syringe is removably mounted. The syringe has a cylinder member which is filled with a liquid. A piston member is slidably inserted into the cylinder member.

Some syringe products are already filled with liquids, and other syringe products allow operators to add desired liquids thereinto. When such a syringe is used in a liquid injector, the syringe is connected through a tank tube to a liquid tank filled with a liquid, and the syringe is mounted on an injection head, by way of example. The injection head separately holds a cylinder member and a piston member of the syringe and moves the piston member rearward from the cylinder member with a slider mechanism.

After the liquid is added into the syringe from the liquid tank, the liquid tank and the tank tube are removed from the syringe which, in turn, is connected to a patient through a patient tube. In this state, the injection heads moves the piston member forward into the cylinder member with the slider mechanism to inject the liquid from the syringe into the patient.

In the conventional liquid injector, however, an operator needs to connect the syringe to the liquid tank through the tank tube when the liquid is sucked from the liquid tank into the syringe, while the operator needs to remove the tank tube from the syringe and connect the patient tube to the syringe when the liquid is injected into the patient from the syringe. This requires complicated operation by the operator and thus raises the concern that the operator might contaminate the tank tube or patient tube.

To solve the abovementioned problem, another liquid injector has a syringe tube connected to a syringe, a tank tube connected to a liquid tank, and a patient tube connected to a patient, in which those tubes are connected through a switching valve. In the liquid injector, a liquid is sucked from the liquid tank into the syringe while the switching valve is manually operated to block the patient tube and connect the tank tube to the syringe tube.

Then, the liquid is injected into the patient from the syringe while the switching valve is manually operated to block the tank tube and connect the patient tube to the syringe tube. In such a liquid injector, since a liquid can be added into a small-capacity syringe from a large-capacity liquid tank, the liquid can be injected into a plurality of patients only by replacing the patient tube with another one.

In the abovementioned liquid injector, however, the operation is complicated since an operator needs to operate manually the switching valve. This may lead to erroneous operation, for example, the operator attempting to inject the liquid into the patient from the syringe while the patient tube is blocked and the tank tube is connected to the syringe tube, or the operator attempting to suck the liquid from the liquid tank into the syringe while the tank tube is blocked and the patient tube is connected to the syringe tube.

To solve the problem, the applicants have proposed a liquid injector which has a syringe tube connected to a syringe, a tank tube connected to a liquid tank, and a patient tube connected to a patient, in which those tubes are connected through a tube connecting means and a one-way valve is provided for each of the tank tube and the patient tube.

In the liquid injector, when an injection head moves a piston member rearward from a cylinder member, the one-way valve for the patient tube is closed and the one-way valve for the tank tube is opened, so that a liquid is sucked from the liquid tank into the syringe. On the other hand, when the injection head moves the piston member forward into the cylinder member, the one-way valve for the tank tube is closed and the one-way valve for the patient tube is opened, so that the liquid is injected into the patient from the liquid.

In the liquid injector, contamination can be prevented only by replacing the patient tube with another one for each patient, and a large amount of liquid in the liquid tank can be injected into patients through the syringe.

In reality, however, the one-way valve is formed in structure to be closed by a backflow of the liquid, so that a slight amount of blood or liquid may flow back into the syringe from the patient and then into the liquid tank from the syringe in the abovementioned liquid injector. In this case, the syringe and the liquid injector are contaminated, which means that the liquid cannot be injected into a plurality of patients even when a large-capacity liquid tank is used.

DISCLOSURE OF INVENTION

The present invention has been made in view of the abovementioned problems, and it is an object of the present invention to provide a liquid injector capable of using a syringe to suck a liquid from a liquid tank and inject the liquid into a patient, and preventing the liquid or blood from flowing back into the syringe or the liquid tank from the patient.

A liquid injector according to the present invention has a patient tube, a syringe tube, a tank tube, a tube connecting means, a syringe drive mechanism, a connection switch mechanism, and an interlock control means. A syringe having a cylinder member and a piston member slidably inserted into the cylinder member is used to suck a liquid from a liquid tank and inject the liquid into a patient.

The patient tube has a leading end connected to the patient, while the syringe tube has a trailing end connected to the syringe. The tank tube has a trailing end connected to the liquid tank. The tube connecting means connects the trailing end of the patient, the leading end of the syringe tube, and the leading end of the tank tube. The syringe drive mechanism relatively moves the cylinder member and/or the piston member to cause the syringe to suck and inject the liquid. The connection switch mechanism switches between a suck state in which the patient tube is blocked and the syringe tube is connected to the tank tube and an injection state in which the tank tube is blocked and the syringe tube is connected to the patient tube. The interlock control means interlocks the operation of the syringe drive mechanism and the operation of the connection switch mechanism.

Thus, in the liquid injector of the present invention, the syringe drive mechanism causes the syringe to suck the liquid from the liquid tank in the suck state in which the connection switch mechanism connects the syringe tube to the tank tube, and the syringe drive mechanism causes the syringe to inject the liquid into the patient in the injection state in which the connection switch mechanism connects the syringe tube to the patient tube. Since the connection switch mechanism blocks the patient tube in the suck state, the liquid or blood does not flow back from the patient into the syringe. Since the tank tube is blocked in the injection state, the liquid or the like does not flow back from the syringe into the liquid tank.

Consequently, contamination of the liquid in the syringe and the liquid tank can be prevented, and the liquid can be injected into a number of patients in turn only by replacing the patient tube with another one without replacing the liquid tank or the syringe, for example.

Various means referred to in the present invention may be any as long as it is formed to realize the function, and for example, can be realized as dedicated hardware which performs a predetermined function, a data processing apparatus which has a predetermined function provided by a computer program, a predetermined function realized inside a data processing apparatus by a computer program, a combination thereof, and the like.

Various components referred to in the present invention do not need to be independent items, and it is possible that a plurality of components is formed as one member, a component is contained as part of another component, and a component shares a portion with another component.

BRIEF DESCRIPTION OF THE DRAWINGS

FIGS. 7a and 7b are front views showing the outer appearance of the front of a connection switch mechanism in a first variation.

BEST MODE FOR CARRYING OUT THE INVENTION

Configuration of Embodiment 1

Figure 1:
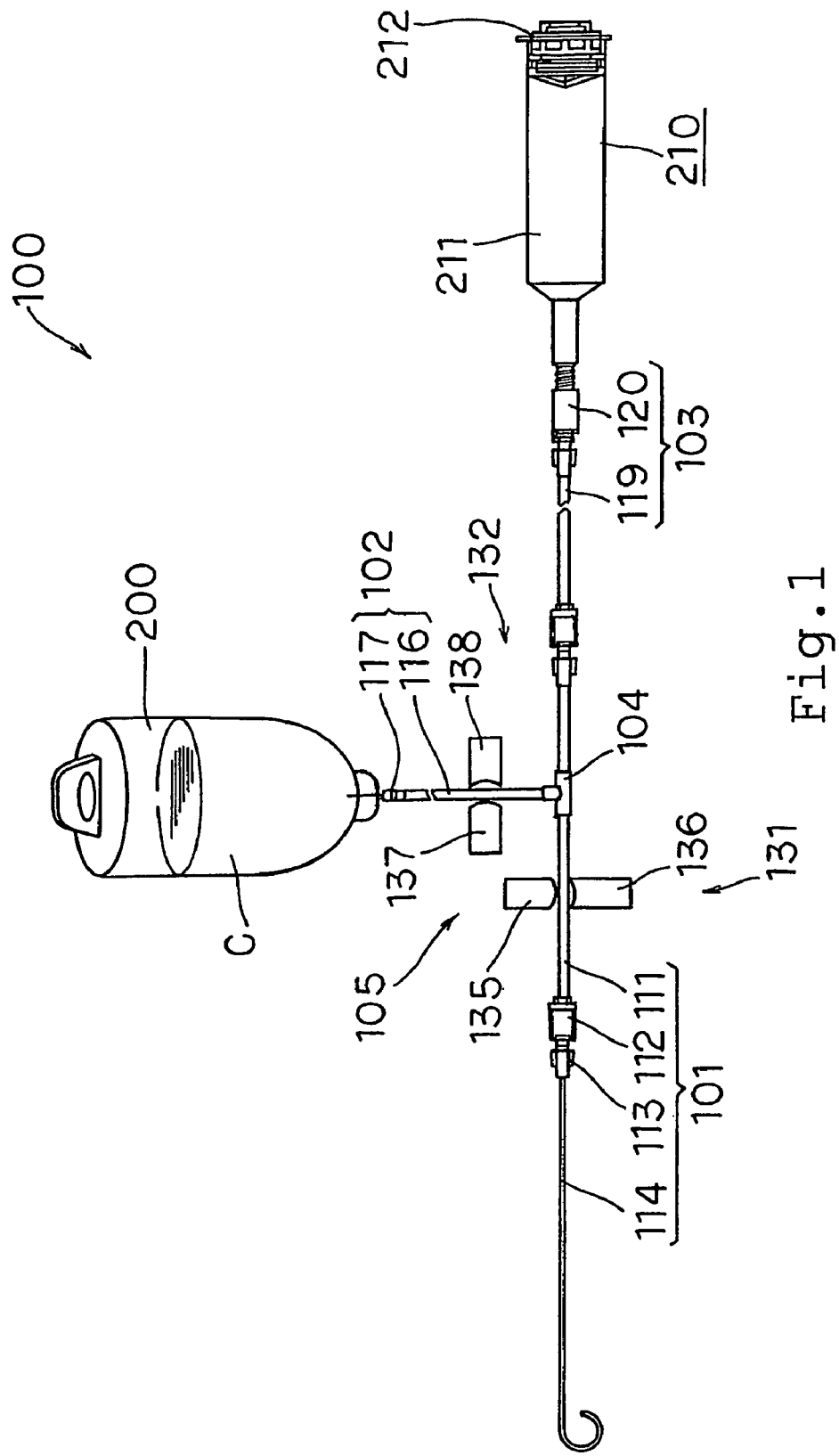
FIG. 1 is a schematic diagram showing the general structure of a liquid injector of Embodiment 1 according to the present invention.

Embodiment 1 of the present invention is hereinafter described with reference to FIGS. 1 to 6. Liquid injector 100 in Embodiment 1 has patient tube 101, tank tube 102, syringe tube 103, tube connecting member 104 serving as a tube connecting means, a syringe drive mechanism (not shown), connection switch mechanism 105, integrative control circuit 106 serving as an interlock control means, operation panel 107, liquid crystal display 108, and the like. As shown in FIG. 1, the trailing end of the patient tube 101, the leading end of the syringe tube 103, and the leading end of the tank tube 102 are connected through tube connecting member 104.

Patient tube 101 is formed of resin tube 111, one-way valve 112, connector 113, and catheter 114, in order from the trailing end to the leading end. Catheter 114 at the leading end is removably connected to a patient (not shown). Resin tube 111 is made, for example, of polyurethane tube containing nylon mesh, and catheter 114 is removably connected to the leading end thereof through connector 113. One-way valve 112 is provided at a position near the leading end of resin tube 111 to regulate the movement of constant medium C serving as a liquid in the direction from resin tube 111 to catheter 114.

Tank tube 102 is formed of resin tube 116 and connector 117 in order from the leading end to the trailing end. Resin tube 116 is also made of polyurethane tube containing nylon mesh, and liquid tank 200 is removably connected to connector 117 at the trailing end. Liquid tank 200 is formed to have a larger capacity than syringe 210 and contains contrast medium C in advance.

Syringe tube 103 is formed of resin tube 119 and connector 120 in order from the leading end to the trailing end. Syringe 210 is removably connected to connector 120 at the trailing end. Syringe 210 is formed of cylinder member 211 and piston member 212 which is slidably inserted into cylinder member 211.

Figure 5:
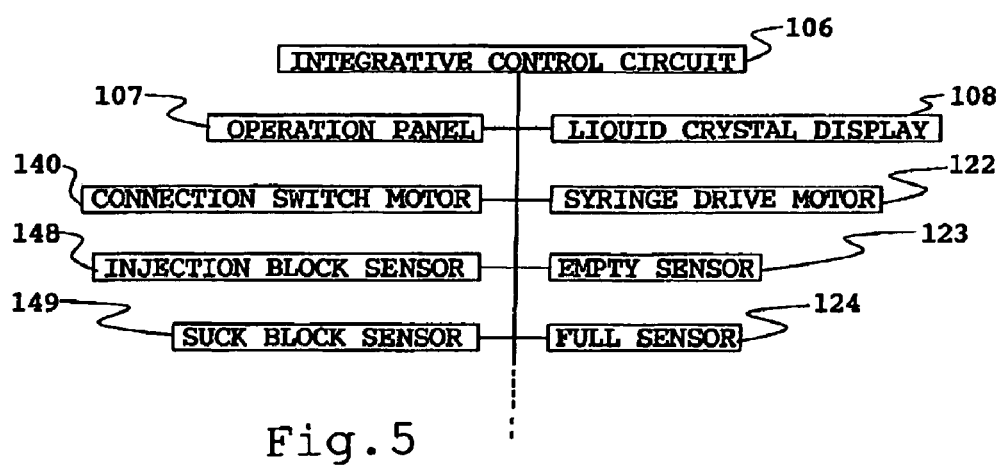
FIG. 5 is a block diagram showing the circuit configuration of the liquid injector.

As shown in FIG. 5, the syringe drive mechanism has syringe drive motor 122, empty sensor 123, and full sensor 124. Syringe 210 connected to syringe tube 103 is removably mounted on the syringe drive mechanism (not shown). The syringe drive mechanism uses syringe drive motor 122 as a drive source to move piston member 212 of syringe 210 while holding cylinder member 211, thereby causing syringe 210 to suck and inject contrast medium C.

Empty sensor 123 senses piston member 212 moving to the leading end of cylinder member 211 to recognize that contrast medium C is not contained in syringe 210. Full sensor 124 senses piston member 212 moving to the trailing end of cylinder member 211 to recognize that contrast medium C is contained in syringe 210 to its full capacity.

Figure 2:
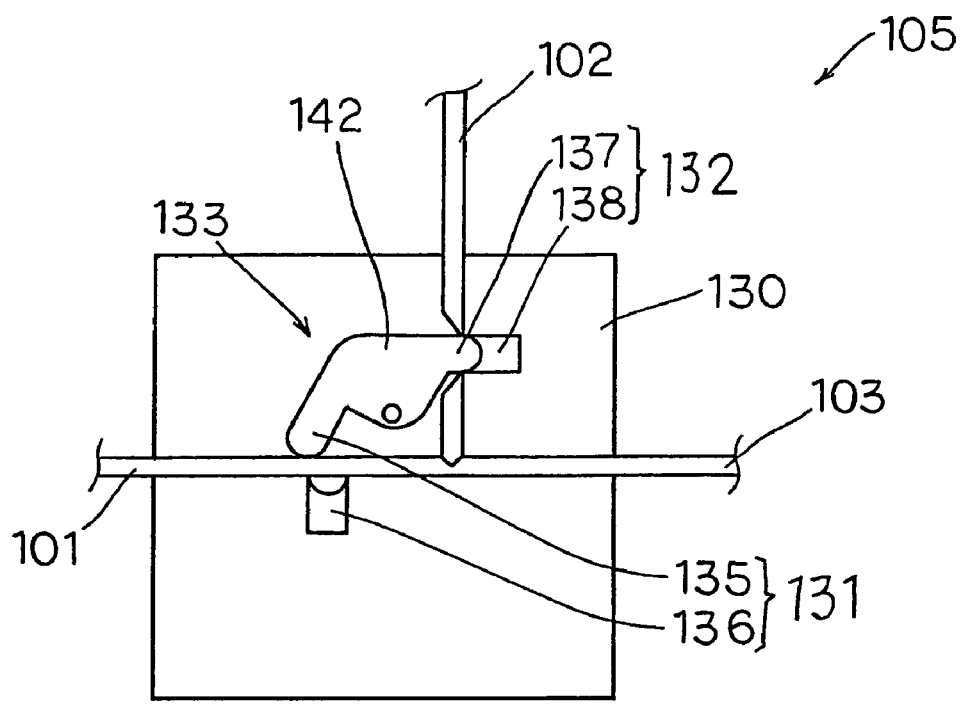
FIG. 2 is a front view showing the outer appearance of the front of a connection switch mechanism.
Figure 3:
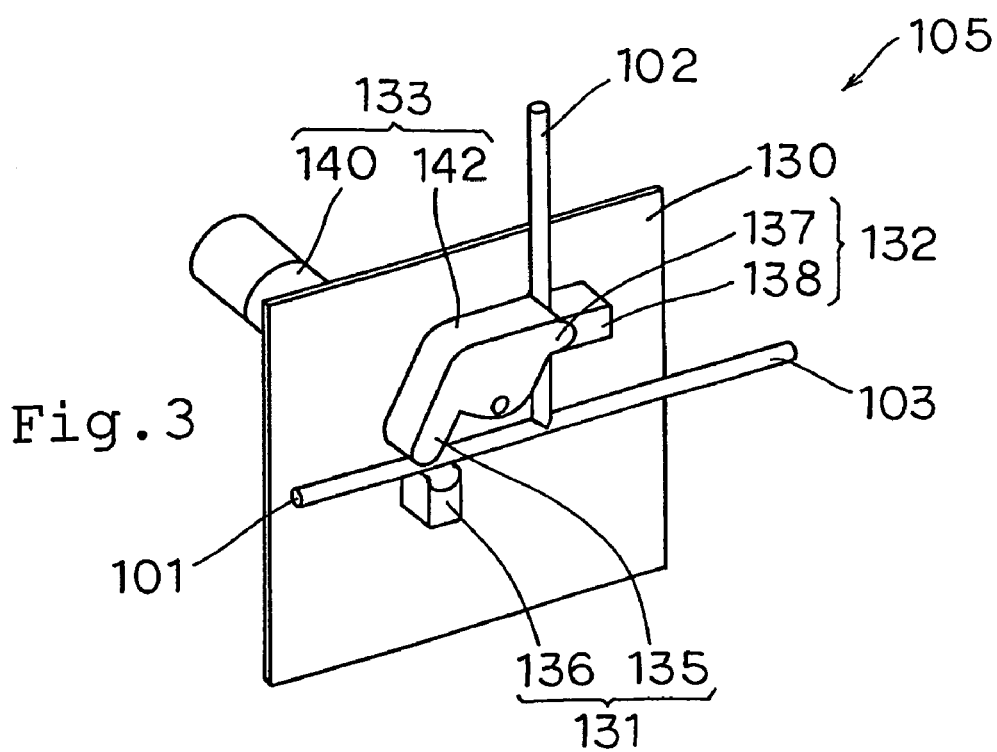
FIG. 3 is a perspective view showing the outer appearance of the front of the connection switch mechanism.
Figure 4:
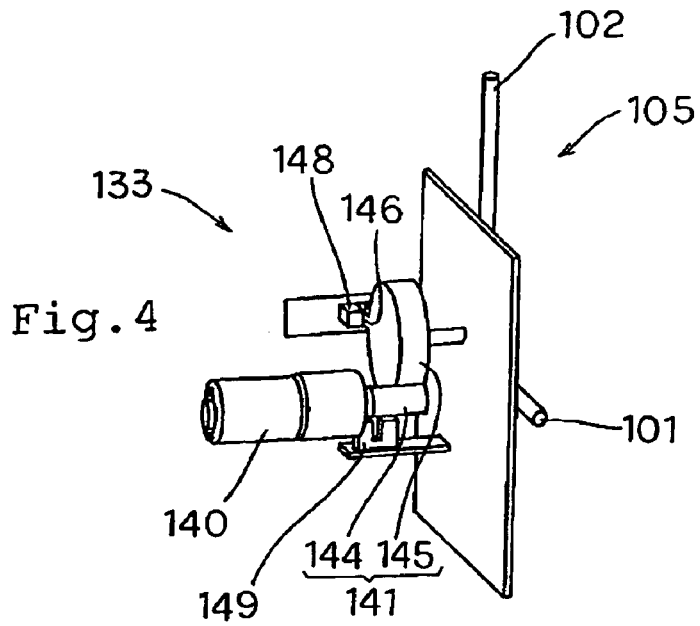
FIG. 4 is a perspective view showing the outer appearance of the back of the connection switch mechanism.

As shown in FIGS. 2 to 4, connection switch mechanism 105 has body panel 130, injection block mechanism 131, suck block mechanism 132, open or close interlock mechanism 133 and the like. Injection block mechanism 131 is formed of injection press member 135 and injection hold member 136. Suck block mechanism 132 is formed of suck press member 137 and suck hold member 138. Open or close interlock mechanism 133 is formed of connection switch motor 140 realized, for example by a stepping motor, gear train 141, and press pivot member 142, in which connection switch motor 140 pivotally supports press pivot member 142 through gear train 141.

Injection press member 135 and suck press member 137 are formed to be integral with press pivot member 142. Injection press member 135 is movably disposed at a position where it presses patient tube 101 when press pivot member 142 is normally rotated. Suck press member 137 is movably disposed at a position where it presses tank tube 102 when press pivot member 142 is reversely rotated.

Injection hold member 136 is disposed opposite to injection press member 135 through patient tube 101, while suck hold member 138 is disposed opposite to suck press member 137 through tank tube 102. Connection switch mechanism 105 switches between a suck state in which patient tube 101 is blocked and syringe tube 103 is connected to tank tube 102 and an injection state in which tank tube 102 is blocked and syringe tube 103 is connected to patient tube 101.

Portions of injection and suck press members 135, 137 for pressing tubes 101, 102, respectively, are formed on convex surfaces which are curved cylindrically. Portions of injection and suck hold members 136, 138 for pressing tubes 101, 102, respectively, are formed on concave surfaces which are curved cylindrically.

Gear train 141 is formed of pinion gear 144 connected directly to connection switch motor 140 and spur gear 145 connected directly to press pivot member 142. Convex 146 is formed on spur gear 145. Injection block sensor 148 realized by a photosensor is disposed at a position for sensing convex 146 in the suck state. Suck block sensor 149 realized by a photosensor is disposed at a position for sensing convex 146 in the injection state. Thus, injection block sensor 148 senses the blocking of patient tube 101, while suck block sensor 149 senses the blocking of tank tube 102.

Integrative control circuit 106 is realized by a microcomputer which has appropriate control programs implemented as firmware. As shown in FIG. 5, operation panel 107, liquid crystal display 108, syringe drive motor 122, empty sensor 123, full sensor 124, connection switch motor 140, injection block sensor 148, suck block sensor 149 and the like are connected to integrative control circuit 106.

Although details are described later, integrative control circuit 106 displays various types of data on liquid crystal display 108 and integrally controls the operation of respective motors 122, 140 in response to data input to operation panel 107 or signals of respective sensors 123, 124, 148, and 149.

Integrative control circuit 106 drives syringe drive motor 122 to suck contrast medium C from liquid tank 200 into syringe 210 after injection block sensor 148 senses the blocking of patient tube 101, and drives syringe drive motor 122 to inject contrast medium C into the patient from syringe 210 after suck block sensor 149 senses the blocking of tank tube 102.

Operation of Embodiment 1

In the configuration as described above, liquid injector 100 of Embodiment 1 is used, for example, to inject contrast medium C serving as the liquid into a patient whose images are created with a CT scanner or an MRI apparatus. In this case, an operator connects patient tube 101 to the patient and connects tank tube 102 to liquid tank 200. In addition, the operator connects syringe tube 103 to syringe 210 which is then loaded on the syringe drive mechanism.

In liquid injector 100 of Embodiment 1, when a patient who is injected with contrast medium C is changed, only catheter 114 of patient tube 101 needs to be changed for each patient while liquid tank 200 and syringe 210 are connected to tank tube 102 and syringe tube 103, respectively, without any change.

Figure 6:
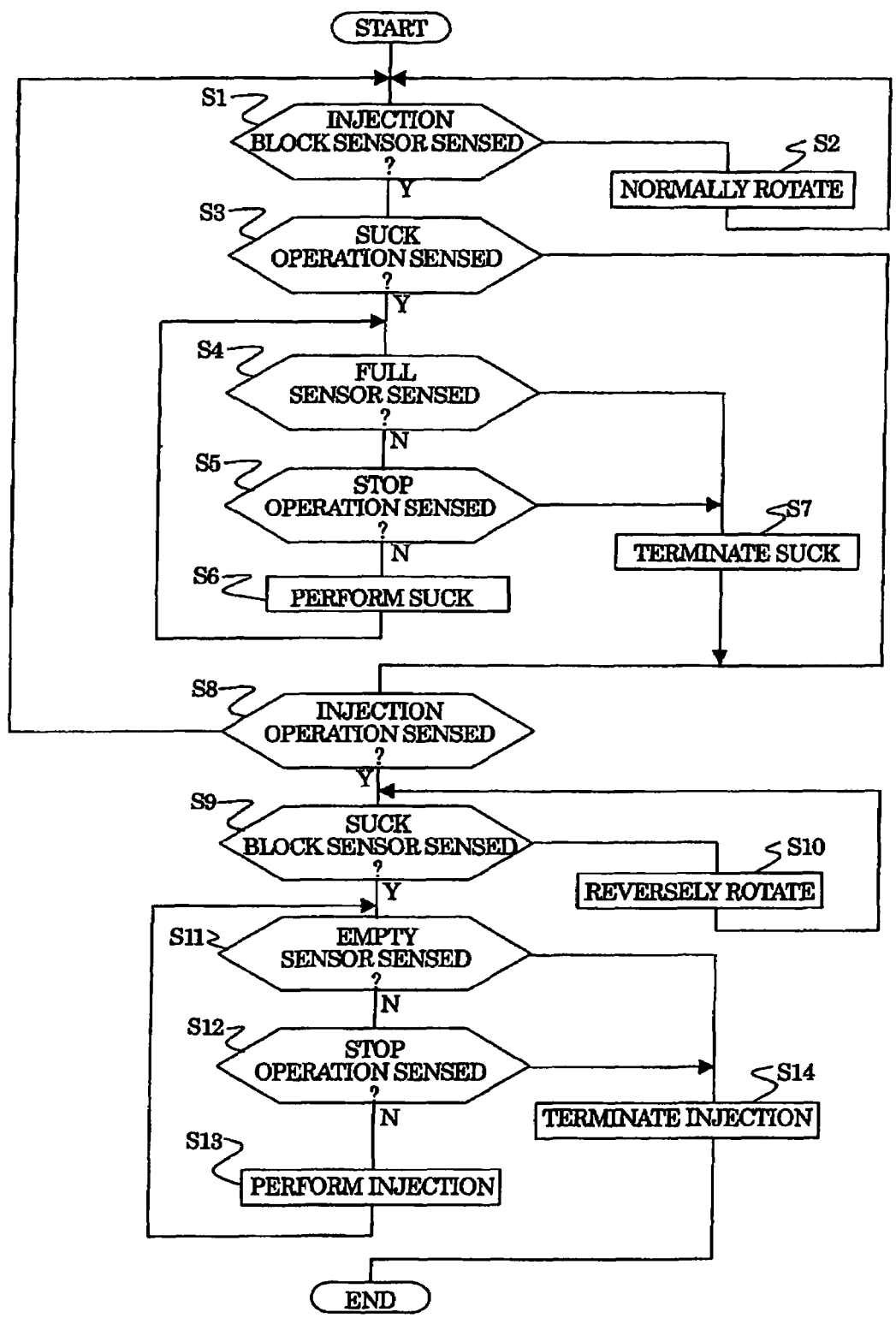
FIG. 6 is a flow chart showing a method of injecting a liquid with the liquid injector.

As shown in FIG. 6, in liquid injector 100 of Embodiment 1, connection switch motor 140 is normally rotated in an initial state until injection block sensor 148 senses the blocking of patient tube 101 (steps S1, S2), thereby blocking patient tube 101.

In this state, when the operator who connected patient tube 101 to the patient makes input to operation panel 107 for sucking or injecting contrast medium C (step S3 or S8), liquid injector 100 performs suck operation or injection operation in response to the input.

For example, when the input is made for sucking (step S3), syringe drive motor 122 is driven to move piston member 212 of syringe 210 rearward from cylinder member 211 while patient tube 101 is blocked as described above (steps S1, S2), and thus contrast medium C is sucked from liquid tank 200 into syringe 210 (step S6).

When full sensor 124 senses piston member 212 being moved rearward to the trailing end (step S5), the drive of syringe drive motor 122 is stopped to terminate the sucking operation of contrast medium C (step S7). Contrast medium C is automatically sucked into syringe 210 to its full capacity.

When the operator who is checking the abovementioned sucking operation makes input to operation panel 107 for stopping the sucking in progress as desired (step S5), however, the drive of syringe drive motor 122 is stopped to terminate the sucking operation of contrast medium C (step S7). In this case, an amount of contrast medium C desired by the operator is sucked into syringe 210.

When input is made to perform injection with contrast medium C contained in syringe 210 as described above (step S8), connection switch motor 140 is reversely rotated until suck block sensor 149 senses the blocking of tank tube 102 (steps S9, S10). In this manner, patient tube 101 is opened and tank tube 102 is blocked.

After the blocking is completed, syringe drive motor 122 is driven to move piston member 212 of syringe 210 forward to inject contrast medium C into the patient from syringe 210 (step S13). When empty sensor 123 senses piston member 212 being moved forward to the leading end (step S11), the drive of syringe drive motor 122 is stopped to terminate the injection operation of contrast medium C (step S14). All of contrast medium C in syringe 210 is automatically injected into the patient.

When the operator who is checking the abovementioned injection operation makes input to operation panel 107 for stopping the injection in progress as desired (step S12), however, the drive of syringe drive motor 122 is stopped to terminate the injection operation of contrast medium C (step S14). In this case, an amount of contrast medium C desired by the operator is injected into the patient. After the injection of contrast medium C is completed as described above, connection switch motor 140 is normally rotated until injection block sensor 148 senses the blocking of patient tube 101 as described above(steps S1, S2), and patient tube 101 is blocked.

Effect of Embodiment 1

In liquid injector 100 of Embodiment 1, since patient tube 101 is reliably blocked by injection block mechanism 131 in the suck state in which contrast medium C is sucked from liquid tank 200 into syringe 210, a backflow of contrast medium C or blood from the patient into syringe 210 can be prevented. In addition, since tank tube 102 is reliably blocked by suck block mechanism 132 in the injection state in which contrast medium C is injected into the patient from syringe 210, a backflow of contrast medium C or the like from syringe 210 into liquid tank 200 can be prevented.

It is thus possible to prevent the contamination of contrast medium C in syringe 210 and liquid tank 200. Contrast medium C can be injected into a number of patients in turn only by replacing catheter 114 of patient tube 101 without replacing liquid tank 200 or syringe 210.

Particularly, in liquid injector 100 of Embodiment 1, the operation of injection block mechanism 131 is interlocked with the operation of the syringe drive mechanism, thereby eliminating erroneous operation, for example, the operator attempting to inject the liquid into the patient from the syringe while patient tube 101 is blocked and tank tube 102 is connected to syringe tube 103, or the operator attempting to suck the liquid from liquid tank 200 into syringe 210 while tank tube 102 is blocked and patient tube 101 is connected to syringe tube 103.

In liquid injector 100 of Embodiment 1, injection block mechanism 131 for blocking patient tube 101 and suck block mechanism 132 for blocking tank tube 102 are formed on one press pivot member 142, so that both of patient tube 101 and tank tube 102 are not blocked or opened.

In liquid injector 100 of Embodiment 1, catheter 114 is connected to resin tube 111 through connector 113 and is easily replaced. In addition, one-way valve 112 is provided at the position near the leading end of resin tube 111, which can prevent a backflow of contrast medium C or blood more reliably.

Since patient tube 101 is automatically blocked by injection block mechanism 131 upon completion of the injection of contrast medium C into the patient from syringe 210, contrast medium C or blood can be prevented from flowing back at all times. Also, since respective tubes 101, 102 are blocked by injection and suck press members 135, 137 and injection and suck hold members 136, 138 with their convex surfaces and concave surfaces on the cylinders, respectively, a backflow of contrast medium C or blood can be prevented more reliably.

In liquid injector 100 of Embodiment 1, one press pivot member 142 is pivoted to switch between the suck state in which patient tube 101 is blocked and the injection state in which tank tube 102 is blocked, which can ensure the switching between the suck state and the injection state with the simple structure.

In liquid injector 100 of Embodiment 1, since connection switch motor 140 for pivoting press pivot member 142 is realized by a stepping motor, press pivot member 142 can be pivoted at a predetermined angle and stopped there. This can reliably maintain the suck state and the injection state with the simple structure.

Variations of Embodiment 1

The present invention is not limited in any way to the abovementioned embodiment, and permits a number of variations without departing from the scope and spirit thereof. For example, while Embodiment 1 has shown patient tube 101, syringe tube 103, and tank tube 102 connected through tube connecting member 104 separate from those tubes, it is possible to form patient tube 101, syringe tube 103, tank tube 102, and tube connecting member 104 as an integral part.

While Embodiment 1 has shown that the portions of injection and suck press members 135, 137 and injection and suck hold members 136, 138 for blocking respective tubes 101, 102 are formed of the convex surfaces and the concave surfaces on the cylinders, they can be planes or S-shaped portions.

In Embodiment 1, one-way valve 112 is provided for patient tube 101 to reliably prevent a backflow of contrast medium C or blood. However, it can be omitted, and a one-way valve (not shown) for regulating the movement of contrast medium C in the direction from liquid tank 200 to syringe 210 can be provided for tank tube 102.

Embodiment 1 has shown connection switch motor 140 realized by the stepping motor to stop press pivot member 142 at a predetermined angle. Alternatively, a lock mechanism (not shown) can be connected to connection switch motor 140 realized by a supersonic motor or the like to stop press pivot member 142 at a predetermined angle, for example.

In connection switch mechanism 105 of Embodiment 1, injection press member 135 of injection block mechanism 131 and suck press member 137 of suck block mechanism 132 are formed to be integral with press pivot member 142 of open or close interlock mechanism 133. However, as in connection switch mechanism 150 shown in FIGS. 7*a* and 7*b*, it is possible to slidably support injection press member 151 and suck press member 152 with a guide rail (not shown) or the like and connect them to crank member 154 of open or close interlock mechanism 153 through injection link member 155 and suck link member 156.

Embodiment 1 has shown that convex 146 of spur gear 145 of open or close interlock mechanism 133 is sensed by injection block sensor 148 and suck block sensor 149. However, as in connection switch mechanism 150 shown in FIGS. 7*a* and 7*b*, convex 157 of crank member 154 can be sensed by injection block sensor 158 and suck block sensor 159 which are realized by mechanical switches.

Figure 8A:
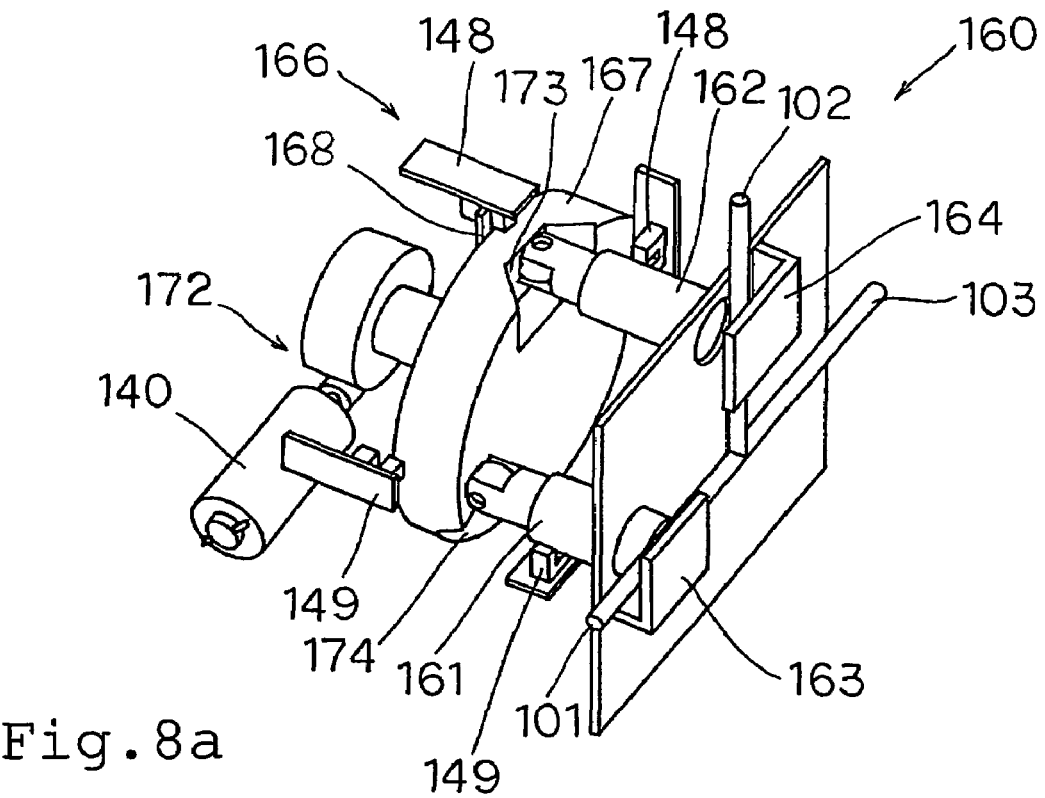
FIGS. 8a and 8b are perspective views showing the outer appearance of a connection switch mechanism in a second variation.
Figure 8B:
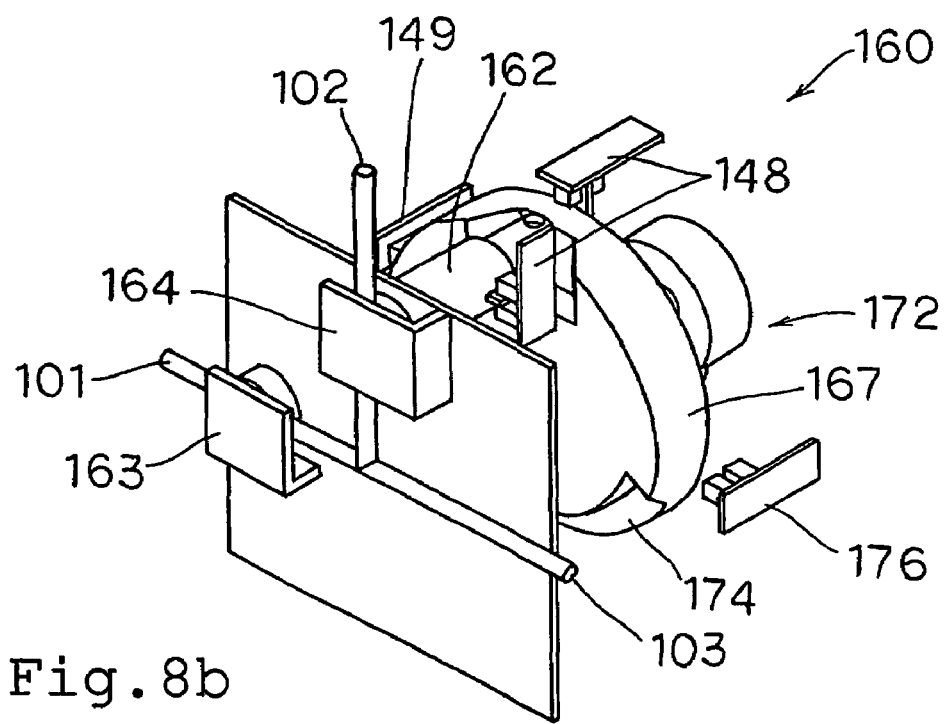
Figure 9:
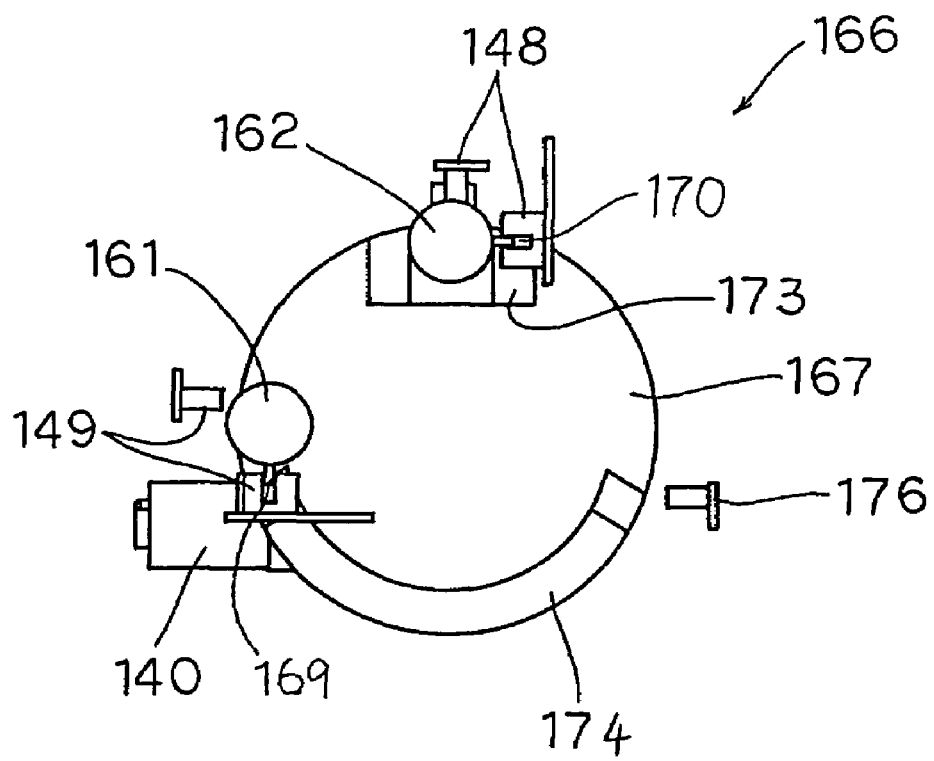
FIG. 9 is a front view showing the outer appearance of the back of the connection switch mechanism in the second variation.

In addition, as in connection switch mechanism 160 shown in FIGS. 8*a*, 8*b*, and 9, it is possible that injection press member 161 and suck press member 162 are supported slidably in the same direction to face injection hold member 163 and suck hold member 164, respectively, and to engage with a surface of rotatable cam member 167 of open or close interlock mechanism 166, on which concaves and convexes are formed.

It is also possible that convex 168 of cam member 167 is sensed by injection block sensor 148 and suck block sensor 149, or convexes 169, 170 of injection press member 161 and suck press member 162 are sensed directly by injection block sensor 148 and suck block sensor 149 as in connection switch mechanism 160.

While Embodiment 1 has shown that connection switch motor 140 is realized by the stepping motor to maintain the suck state and the injection state, the suck state and the injection state can be maintained by forming gear train 172 of worm gears as in connection switch mechanism 160 shown in FIGS. 8a, 8b, and 9.

In connection switch mechanism 160, the trailing ends of injection and suck press members 161, 162 are positioned at concave 173 of the surface of cam member 167 to release the blocking of respective tubes 101, 102, respectively. Thus, after one of them is completely blocked, the blocking of the other can be released, so that a backflow of contrast medium C or the like can be prevented without fail.

In addition, since concave 174 at which both of injection and suck press members 161, 162 are simultaneously located is also formed on cam member 167 in connection switch mechanism 160, the blocking of respective tubes 101, 102 can be released simultaneously as desired, and respective tubes 101, 102 can be easily loaded.

To ensure such operation, convexes 169, 170 of injection press member 161 and suck press member 162 are preferably sensed directly by injection block sensor 148 and suck block sensor 149 described above. However, it is possible to provide dedicated release sensor 176 for sensing both of injection and suck press members 161, 162 being positioned in concave 174.

Figure 10:
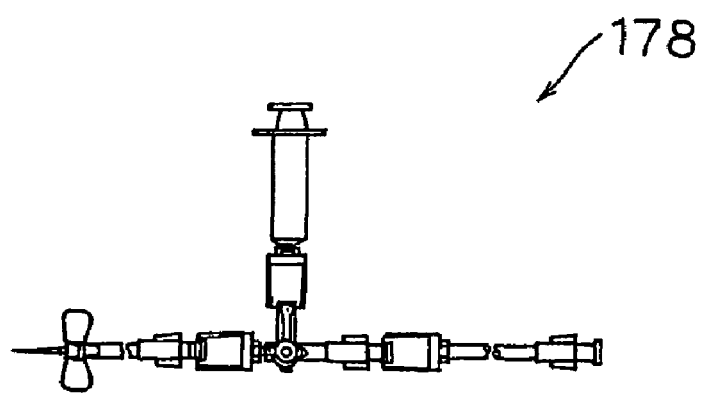
FIG. 10 is a front view showing the outer appearance of a needle.

While Embodiment 1 has shown that the leading end of patient tube 101 is formed of catheter 114, it can be formed of butterfly needle 178 as shown in FIG. 10. Particularly, in liquid injector 100 of Embodiment 1, catheter 114 of patient tube 101 is connected to resin tube 111 through connector 113, it can be replaceable with butterfly needle 178.

While Embodiment 1 has shown the liquid realized by contrast medium C, it can be a drug or saline. It is also possible that contrast medium C and saline W can be freely injected as in liquid injector 300 shown in FIG. 11.

Configuration of Embodiment 2

Figure 11:
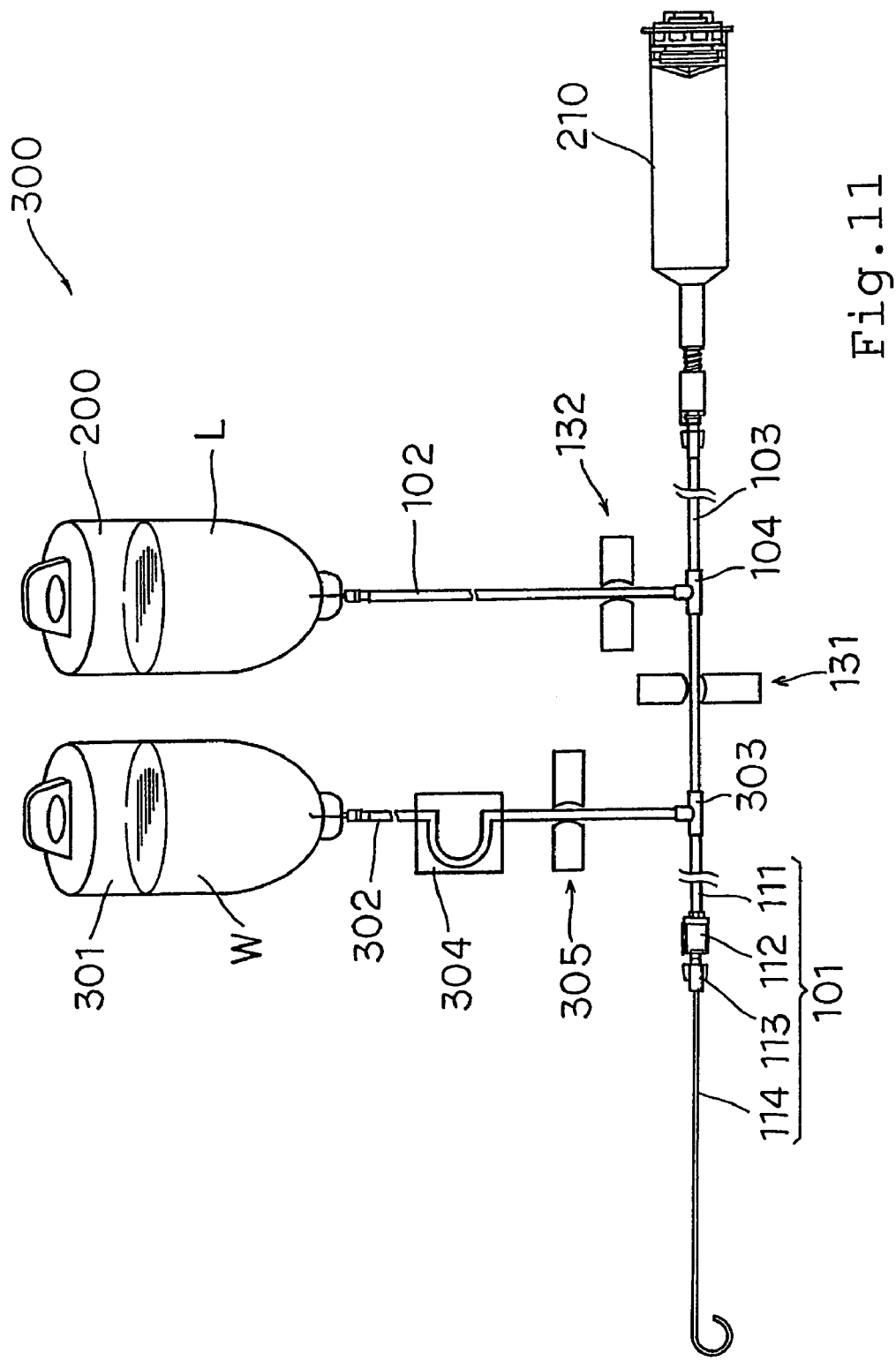
FIG. 11 is a schematic diagram showing the general structure of a liquid injector of Embodiment 2.

Liquid injector 300 described above is hereinafter described briefly as Embodiment 2 with reference to FIG. 11. In liquid injector 300 of Embodiment 2, saline W which is a solution with lower viscosity than contrast medium C is contained in solution tank 301 which is connected to the trailing end of attachment tube 302.

The leading end of attachment tube 302 is connected to resin tube 111 of patient tube 101 through tube connecting member 303 serving as a tube attaching means. Injection block mechanism 131 is positioned between tube connecting members 104, 303 on resin tube 111.

Roller pump 302 serving as a solution injection device and attachment block mechanism 305 are positioned in order from the trailing end to the leading end of attachment tube 302. They are also connected to integrative control circuit 106 (not shown). Roller pump 304 injects saline W in solution tank 301 into a patient. Attachment block mechanism 305 presses and blocks attachment tube 302 to freely open or close attachment tube 302. Integrative control circuit 106 causes attachment block mechanism 305 to release the blocking only when connection switch mechanism 105 blocks patient tube 101, and causes roller pump 304 to operate only when the blocking by attachment block mechanism 305 is released.

Operation of Embodiment 2

In liquid injector 300 of Embodiment 2, contrast medium C and saline W can be freely injected into the patient. Specifically, the blocking by Attachment block mechanism 305 is released and roller pump 304 is operated only when connection switch mechanism 105 blocks patient tube 101.

Effect of Embodiment 2

As a result, in liquid injector 300 of Embodiment 2, contrast medium C, saline W, or blood does not flow back from the patient into solution tank 301 and liquid tank 200, saline W does not move into liquid tank 200 from solution tank 301, or contrast medium C does not move into solution tank 301 from liquid tank 200 or syringe 210.

Variations of Embodiment 2

While Embodiment 2 has shown the structure in which the leading end of attachment tube 302 is connected at the position between the leading end of patient tube 101 and injection block mechanism 131, it is possible that the leading end of attachment tube 302 is connected to a position between injection block mechanism 131 on patient tube 101 and tube connecting member 104, for example.

It is also possible that a second injection block mechanism (not shown) is additionally provided at a position between the leading end of patient tube 101 and tube connecting member 303. In the structure, roller pump 304 can be omitted to suck and inject saline W with syringe 210.

Configuration of Embodiment 3

Figure 12:
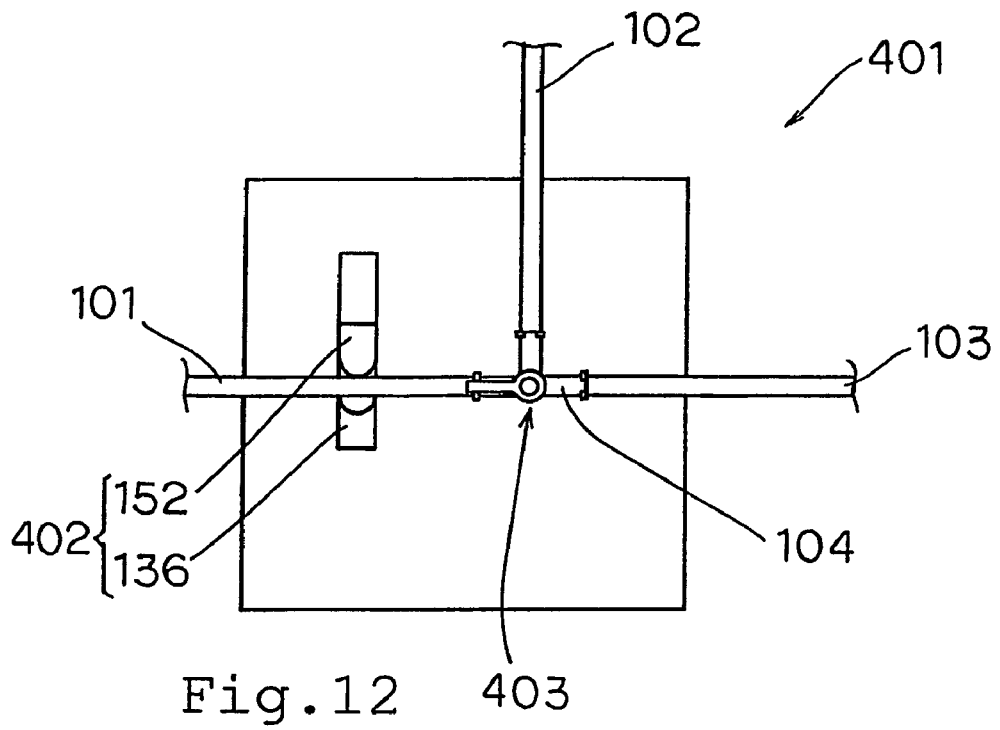
FIG. 12 is a front view showing the outer appearance of the front of a connection switch mechanism of the liquid injector of Embodiment 2.
Figure 13:
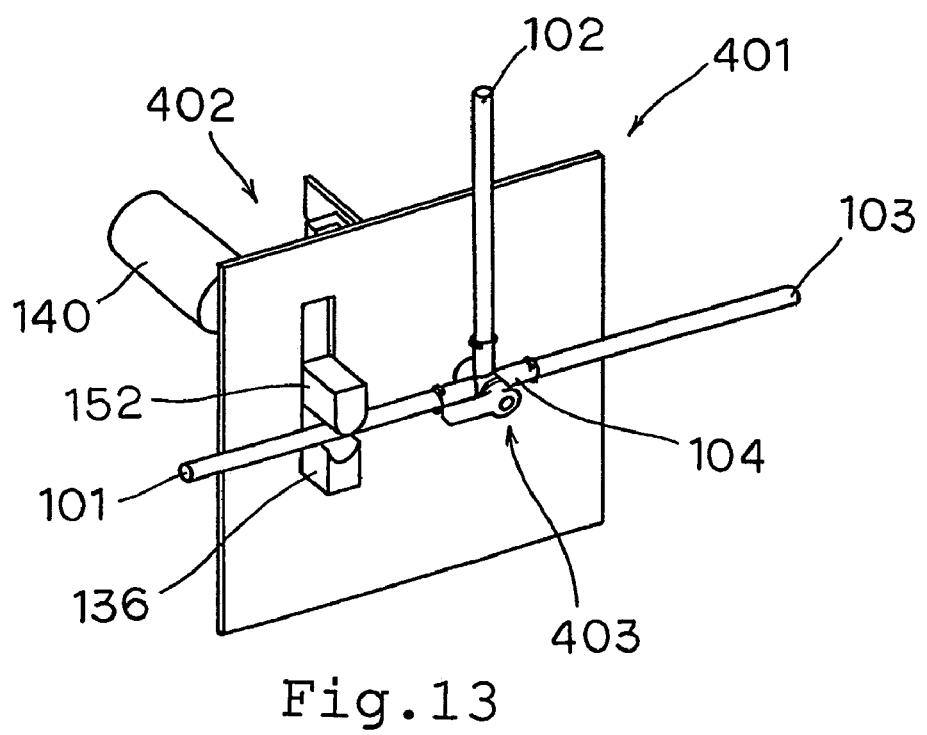
FIG. 13 is a perspective view showing the outer appearance of the front of the connection switch mechanism.
Figure 14:
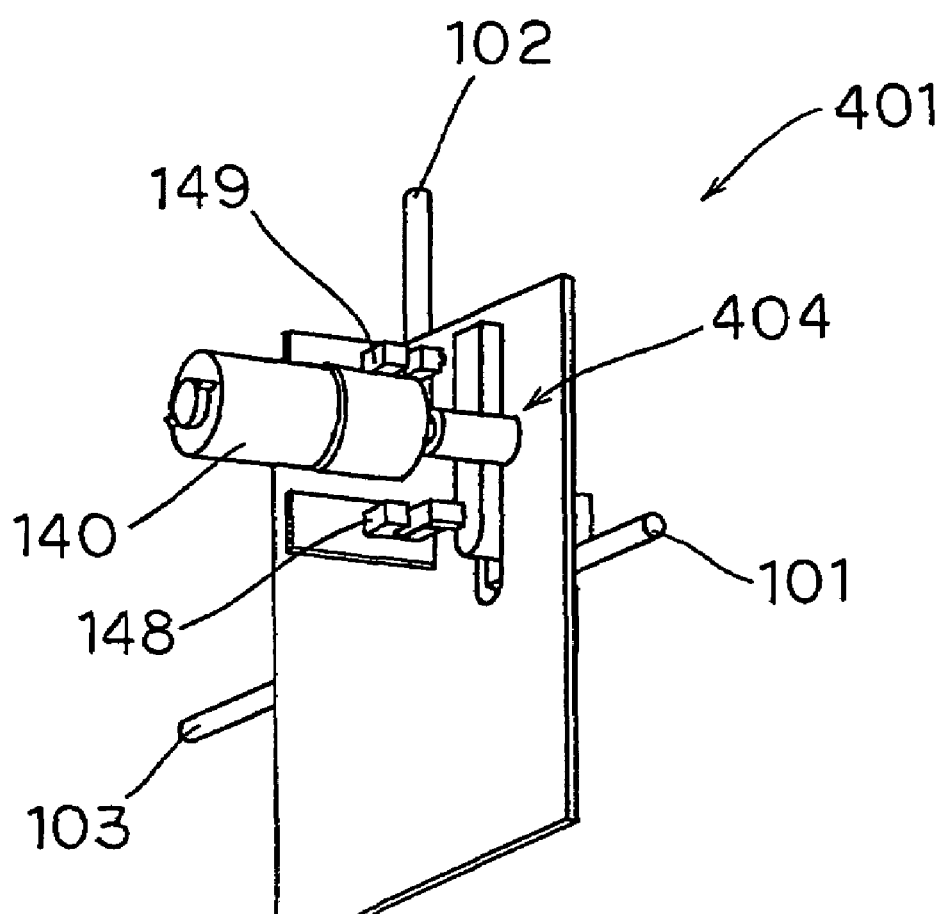
FIG. 14 is a perspective view showing the outer appearance of the back of the connection switch mechanism.

Embodiment 3 of the present invention is hereinafter described briefly with reference to FIGS. 12 to 14. In a liquid injector (not shown) of Embodiment 3, connection switch mechanism 401 is formed of injection block mechanism 402 and switching valve 403 which is provided at the position of tube connecting member 104.

Injection press member 152 of injection block mechanism 402 is connected to connection switch motor 140 with rack and pinion mechanism 404. A switch sensor (not shown) is connected to switching valve 403. The switch sensor is connected to integrative control circuit 106 (not shown) which integrally controls the respective parts in accordance with output from the switch sensor.

Operation of Embodiment 3

In the liquid injector of Embodiment 3, when an operator manually operates switching valve 403 as desired, switching valve 403 switches between the suck state and the injection state, and the switch operation of switching valve 403 is sensed by the switch sensor and then recognized by integrative control circuit 106.

Integrative control circuit 106 causes injection block mechanism 402 to block patient tube 101 to permit the suck operation of a syringe drive mechanism when switching valve 403 is switched to the suck state. When switching valve 403 is switched to the injection state, integrative control circuit 106 causes injection block mechanism 402 to open patient tube 101 to permit the injection operation of the syringe drive mechanism.

Effect of Embodiment 3

In the liquid injector of Embodiment 3, switching valve 403 is manually operated to integrally control the respective parts such as injection block mechanism 402 to set switching between the suck state and the injection state, so that the switching between the suck state and injection state can be reliably achieved with intuitively recognizable and simple operation.

Variations of Embodiment 3

While Embodiment 3 has shown that switching valve 403 is used as the operation switch to interlock the operation of injection block mechanism 402 and the like, it is possible that a drive motor (not shown) is connected to switching valve 403, and a separate operation switch is manually operated to interlock the operation of switching valve 403 and the operation of injection block mechanism 402, for example.

The invention claimed is:

1. A liquid injector for causing a syringe to suck a liquid from a liquid tank and inject the liquid into a patient, the syringe having a cylinder member and a piston member inserted slidably into the cylinder member, comprising:
   a patient tube having a leading end connected to the patient;
   a syringe tube having a trailing end connected to the syringe;
   a tank tube having a trailing end connected to the liquid tank;
   a tube connecting means for connecting a trailing end of the patient tube, a leading end of the syringe tube, and a leading end of the tank tube;
   a syringe drive mechanism for relatively moving the cylinder member and/or the piston member to cause the syringe to suck and inject the liquid;
   a connection switch mechanism for switching between a suck state in which the patient tube is blocked and the syringe tube is connected to the tank tube and an injection state in which the tank tube is blocked and the syringe tube is connected to the patient tube;
   an interlock control means for interlocking operation of the syringe drive mechanism and operation of the connection switch mechanism; and
   an attachment tube having a trailing end connected to a solution injector for injecting a solution into the patient, tube attaching means for attaching a leading end of the attachment tube to the patient tube, and an attachment block mechanism for pressing and blocking the attachment tube to freely open or close the attachment tube,
   wherein the interlock control means causes the attachment block mechanism to release the blocking only when the connection switch mechanism blocks the patient tube.

2. The liquid injector according to claim 1, wherein the connection switch mechanism has an injection block mechanism for pressing the patient tube to freely open or close the patient tube.

3. The liquid injector according to claim 2, wherein the connection switch mechanism also has a switching valve provided at the position of the tube connecting means.

4. The liquid injector according to claim 2, wherein the connection switch mechanism also has a suck block mechanism for pressing the tank tube to freely open or close the tank tube.

5. The liquid injector according to claim 4, wherein the connection switch mechanism also has an open or close interlock mechanism for interlocking open and close operation of the injection block mechanism and the suck block mechanism such that one of them performs open operation when the other performs close operation.

6. The liquid injector according to claim 5, wherein the injection block mechanism has an injection press member movably disposed at a position for pressing the patient tube and an injection hold member disposed opposite to the injection press member through the patient tube,
   the suck block mechanism has a suck press member movably disposed at a position for pressing the tank tube and a suck hold member disposed opposite to the suck press member through the tank tube, and
   the open or close interlock mechanism has a press pivot member having the injection press member and the suck press member formed integrally and supported pivotally.

7. The liquid injector according to claim 5, wherein the injection block mechanism has an injection press member slidably supported at a position for pressing the patient tube and an injection hold member disposed opposite to the injection press member through the patient tube,
   the suck block mechanism has a suck press member slidably supported at a position for pressing the tank tube and a suck hold member disposed opposite to the suck press member through the tank tube, and
   the open or close interlock mechanism has a crank member pivotally supported on its own trailing end, an injection link member for connecting a leading end of the crank member to the injection press member, and a suck link member for connecting the leading end of the crank member to the suck press member.

8. The liquid injector according to claim 5, wherein the injection block mechanism has an injection press member slidably supported at a position for pressing the patient tube and an injection hold member disposed opposite to the injection press member through the patient tube,
   the suck block mechanism has a suck press member slidably supported at a position for pressing the tank tube and a suck hold member disposed opposite to the suck press member through the tank tube, and
   the open or close interlock mechanism has a cam member pivotally supported and having a concave and a convex with which the injection press member and the suck press member engage.

9. The liquid injector according to claim 2, wherein the interlock control means causes the injection block mechanism to block the patient tube when the injection by the syringe drive mechanism is completed.

10. The liquid injector according to claim 1, further comprising an injection block sensor for sensing the patient tube being blocked and a suck block sensor for sensing the tank tube being blocked,
    wherein the interlock control means causes the syringe drive mechanism to perform the suck after the injection block sensor senses the blocking and causes the syringe drive mechanism to perform the injection after the suck block sensor senses the blocking.

11. The liquid injector according to claim 1, further comprising a one-way valve for regulating the movement of the liquid from the syringe to the patient, the one-way valve being provided for the patient tube.

12. The liquid injector according to claim 1, further comprising a one-way valve for regulating the movement of the liquid from the liquid tank to the syringe, the one-way valve being provided for the tank tube.

13. The liquid injector according to claim 1, wherein the tube attaching means attaches the leading end of the attachment tube to a portion between the leading end of the patient tube to the connection switch mechanism.

* * * * *